US00PP10199P

United States Patent [19]

Egger et al.

[11] Patent Number: Plant 10,199

[45] Date of Patent: Jan. 13, 1998

[54] ASIATIC HYBRID LILY PLANT NAMED 'CEB JEWEL'

[75] Inventors: Donald L. Egger, Wilsonville; Edward A. McRae, Sandy, both of Oreg.

[73] Assignee: Cebeco Lilies, Inc., Aurora, Oreg.

[21] Appl. No.: 691,040

[22] Filed: Aug. 7, 1996

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Klarquist Sparkman Campbell Leigh & Whinston, LLP

[57] ABSTRACT

A new and distinct Lily Hybrid having numerous, large, unspotted, warm pink flowers with a gold blush on short, strong stems excellent for pot plant production.

1 Drawing Sheet

BACKGROUND OF THE INVENTION

The present invention relates to a new and distinct cultivar of Lily hybrid referred to commercially as an Asiatic hybrid pot lily and named 'Ceb Jewel'. This invention was developed by controlled breeding in Aurora, Oregon using OF-98×(OB-8×OA-11), a proprietary, non-released plant as the seed parent, and 8–80, another proprietary non-released plant as the pollen parent.

This invention has not been observed under all possible environmental conditions. The phenotype may vary significantly with variations in environment such as temperature, light intensity, and day length, without, however, any variation in genotype.

The following traits have been repeatedly observed and are determined to be the basic characteristics of this invention which in combination distinguish this lily as a new and distinct cultivar: 1) large, warm pink flowers with a gold blush and no spots; 2) short, strong stems with nice quality foliage making an excellent pot subject; 3) excellent inflorescence and flower number; 4) very early bloom time; 5) long lasting flowers; 6) true dwarf plant requiring no growth regulators; and 7) uniform stems. Bulbs of this plant may be precooled and forced out of season for very uniform pot plant production. In addition, this new lily shows good disease tolerance.

Of the many commercial cultivars known to the present inventor, the only comparison to this new cultivar is 'Denia'. This invention has better flower color, larger flowers, no spots, and shorter stems.

Asexual reproduction of this new variety has been accomplished at Cebeco Lilies, Inc., in Aurora, Ore., by scaling and tissue culture. The resulting plants have shown that the above-mentioned unique features are stable and reproduce true to type in each successive propagation.

Figure 2:
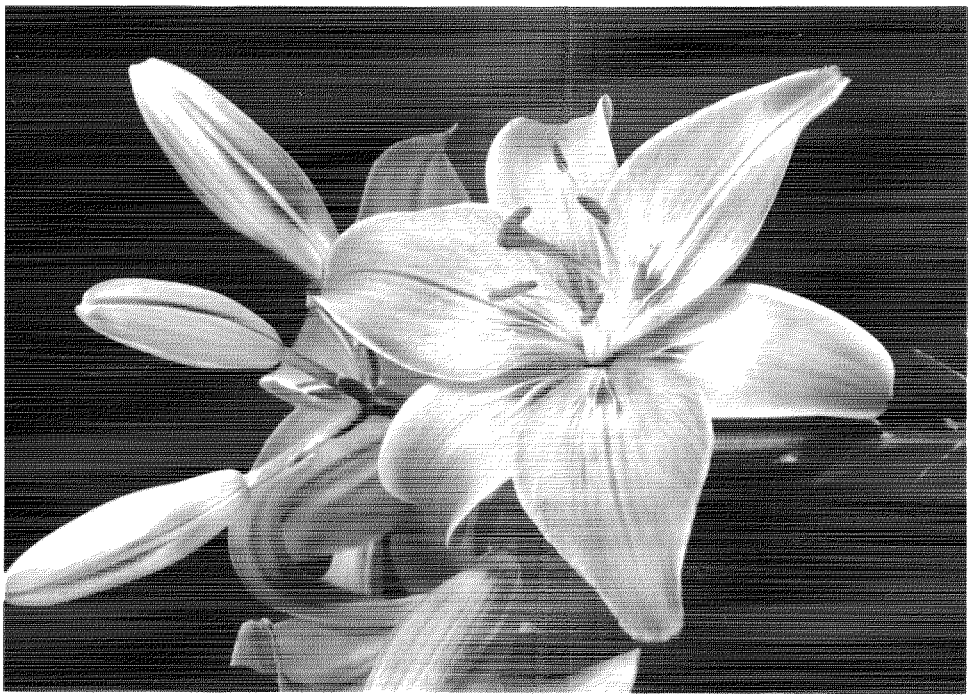
FIG. 2 is a close-up photograph which illustrates in greater detail a single flower of the new plant.
Figure 1:
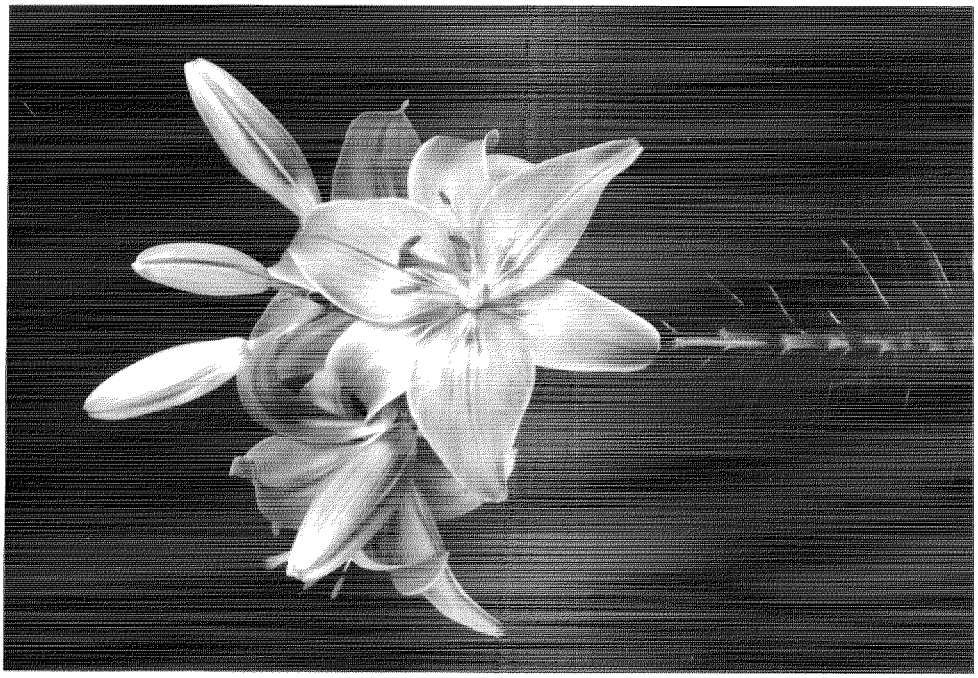
FIG. 1 is a photograph showing the 'Ceb Jewel' lily.

The photographs of the drawing were taken in August 1993 in a studio and illustrate the typical flower and foliage form, with color as true as reasonably possible in this type of color photograph.

DETAILED DESCRIPTION

The following is a detailed description of the invention based on plants produced under commercial practices in the Cebeco Lilies, Inc. greenhouses in Aurora, Ore. in Jul. 1993. Color references are made to The Royal Horticultural Society Colour Chart, except where the context indicates a term having its ordinary dictionary meaning.

THE PLANT

Origin: Seedling.

Parentage:

*Seed parent.*—OF-98×(OB-8×OA-11) .

*Pollen parent.*—8–80.

Commercial classification: Hybrid Asiatic Lily, pot type.

Classification: Division I-ab, Asiatic Hybrid Lily, upright flowering and outward flowering, according to the Horticultural Classification of Lilies by The Royal Horticultural Society of London.

Form: Single erect stem bearing terminal cluster of flowers.

Height: About 37 cm. from the top of the soil to the top of the flowers from bulbs of 10–12 cm. in circumference.

Growth habit: Vigorous, upright and rigid.

Foliage:

*Arrangement.*—Spiral.

*Quantity.*—Dense.

*Leaf size.*—Small. From about 6–7 cm. long and about 6–8 mm. wide.

*Leaf shape.*—Linear with entire margins.

*Texture.*—Leathery.

*Aspect.*—Glossy.

*Color.*—Medium green on both sides. Yellow-Green Group 147A.

Bulbs:

*Size.*—Variable, ranging to about 10–14 cm. in circumference as used commercially.

*Color.*—White.

THE BUD

Size: Large, to about 7 cm. long and 23 mm. wide just prior to opening.

Shape: Ovoid with an obtuse tip.

Rate of opening: The mature bud opens slowly in response to light.

Color: Warm pink, Red Group 54A, with lime green, Yellow-Green Group 144B-C at the ends and midrib.

THE FLOWER

Blooming habit: Annually, once and early season.

Days to bloom: Flowers approximately 56 days after spring greenhouse planting under typical commercial flower forcing conditions of 15 degrees Celsius night time temperatures.

Inflorescence size: About 9 cm. high and 18 cm. wide when there are five flowers present.

Flower Size: Large.

*Diameter.*—About 14 cm.

*Depth.*—About 3 cm.

Borne: In an umbel or modified raceme of 6 flowers from bulbs 10–12 cm. in circumference.

Shape: When the flower first opens it is bowl shaped. Later the shape flattens out and the tepals reflex slightly at the tips.

Tepalage:

*Number.*—Six.

*Arrangement.*—Imbricated.

*Shape.*—Ovate.

*Texture.*—Spongy, waxy.

*Aspect.*—Satiny.

*Size.*—Length: About 8 cm. Width: Inner tepals — about 42 mm. Outer tepals — about 28 mm.

Depth of imbrication: About 10 mm.

Nectary: About 2 cm. long; yellow green to warm pink; sparsely papillose; with the channels apart at the top.

Projections: Few, alongside nectary, as raised lines.

Spots: None.

Blush: Above the nectary like a spot, gold, Yellow Group 13B-C, and fading to white with age.

Color:

*Topside.*—Warm Pink. Red Group 54A at tip where it is darkest to Red Group 55A (lightening to 55C or D in an old flower) with a gold blush as described above.

*Bottomside.*—Warm pink. Red Group 54A.

Discoloration: Lightens with age.

Fragrance: None.

Lasting quality: Excellent.

Pedicle:

*Length.*—Vary from 2.5 to 3.5 cm.

*Color.*—Yellow green (144A) overlaid with maroon spots, Grayed-Purple Group 185A-183A.

*Orientation.*—Wide at the bottom of the inflorescence. Ascending upwardly from about 85°–45° from the horizontal.

THE REPRODUCTIVE ORGANS

Stamens:

*Number.*—Six, typical of the genus Lilium.

*Anthers before dehiscence.*—Size: About 2 cm. Color: Rust. Greyed-Orange Group 167B.

*Filaments.*—Length: About 5.5 cm. Color: Pink, Red Group 54D near top and white on bottom half.

Pollen:

*Color.*—Rust. Greyed-Orange Group 167A.

Pistil:

*Number.*—One.

*Style.*—Length: About 6 cm. Color: Warm pink, Red Group 54B on top and creamy yellow, Yellow-Green Group 150D on bottom.

*Stigma.*—Color: Purple. Greyed-Purple Group 186A.

THE FRUIT

Fertility: Fertile.

Shape: Ovoid.

Color at Maturity: Soft brown.

I claim:

1. A new and distinct cultivar of Asiatic hybrid lily plant substantially as herein shown and described.

* * * * *